United States Patent
Ladner

(10) Patent No.: US 10,139,328 B2
(45) Date of Patent: Nov. 27, 2018

(54) APPARATUS FOR GAUGING LIQUID OR SOLID MASS CONTAINED IN A VESSEL AND METHOD FOR USING SAME

(71) Applicant: Daniel Ray Ladner, Boulder, CO (US)

(72) Inventor: Daniel Ray Ladner, Boulder, CO (US)

(*) Notice: Subject to any disclaimer, the term of this patent is extended or adjusted under 35 U.S.C. 154(b) by 1136 days.

(21) Appl. No.: 13/999,664

(22) Filed: Mar. 14, 2014

(65) Prior Publication Data

US 2014/0260622 A1 Sep. 18, 2014

Related U.S. Application Data

(60) Provisional application No. 61/852,184, filed on Mar. 15, 2013.

(51) Int. Cl.
| | |
|---|---|
| G01N 9/00 | (2006.01) |
| G01H 13/00 | (2006.01) |
| G01H 3/08 | (2006.01) |
| G01F 15/00 | (2006.01) |
| G01F 15/18 | (2006.01) |

(52) U.S. Cl.
CPC .......... *G01N 9/002* (2013.01); *G01F 15/007* (2013.01); *G01F 15/18* (2013.01); *G01H 3/08* (2013.01); *G01H 13/00* (2013.01)

(58) Field of Classification Search
CPC .............................. G01N 9/002; G01N 29/12
See application file for complete search history.

(56) References Cited

PUBLICATIONS

Ladner et al., Low-Gravity MAss GAuging System (MAGA), Jan. 2012.*

* cited by examiner

*Primary Examiner* — Erika J Villaluna

(57) ABSTRACT

The invention enables determination of an unknown fluid mass contained within a vessel by measuring the resonant frequency response of the vessel and its support structure when an excitation source is activated. The excitation produces a relative displacement between the fluid containment vessel and its support structure which comprise a spring/mass system. The displacement produces signal voltages in one or more attached sensors. The frequency and amplitude of the sensor signals vary in accordance with physical principles that relate the amplitude and the frequency of vibrations to the masses and spring constants of the spring/mass system. Alternatively, determination of the resonant frequency from measurements of the relative displacement of the vessel and its support structure vs. time using a positioning device can be used to determine the unknown mass. For a given mass of fluid the resulting amplitudes and resonant frequency modes are identical even if the fluid secondary properties are different.

20 Claims, 8 Drawing Sheets

FIGURE 1a. Side view of a cylindrical vessel showing the primary mechanical components and devices for frequency excitation and measurement.

Axis of Symmetry — Side View

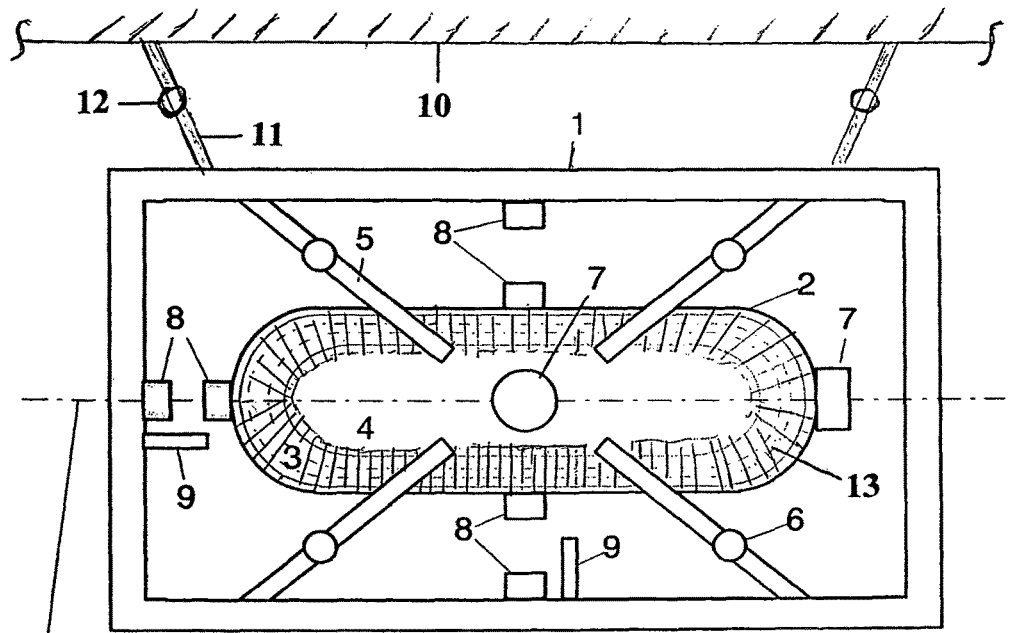
FIGURE 1a. Side view of a cylindrical vessel showing the primary mechanical components and devices for frequency excitation and measurement.
Side View
Axis of Symmetry
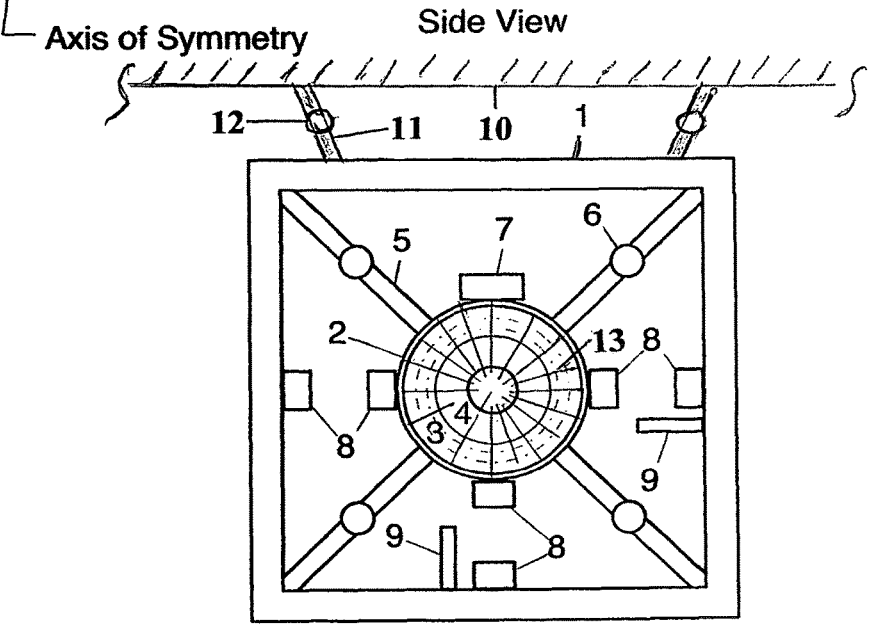
FIGURE 1b. End view of a cylindrical vessel or side view of a spherical vessel showing the primary mechanical components and devices for frequency excitation and measurement.

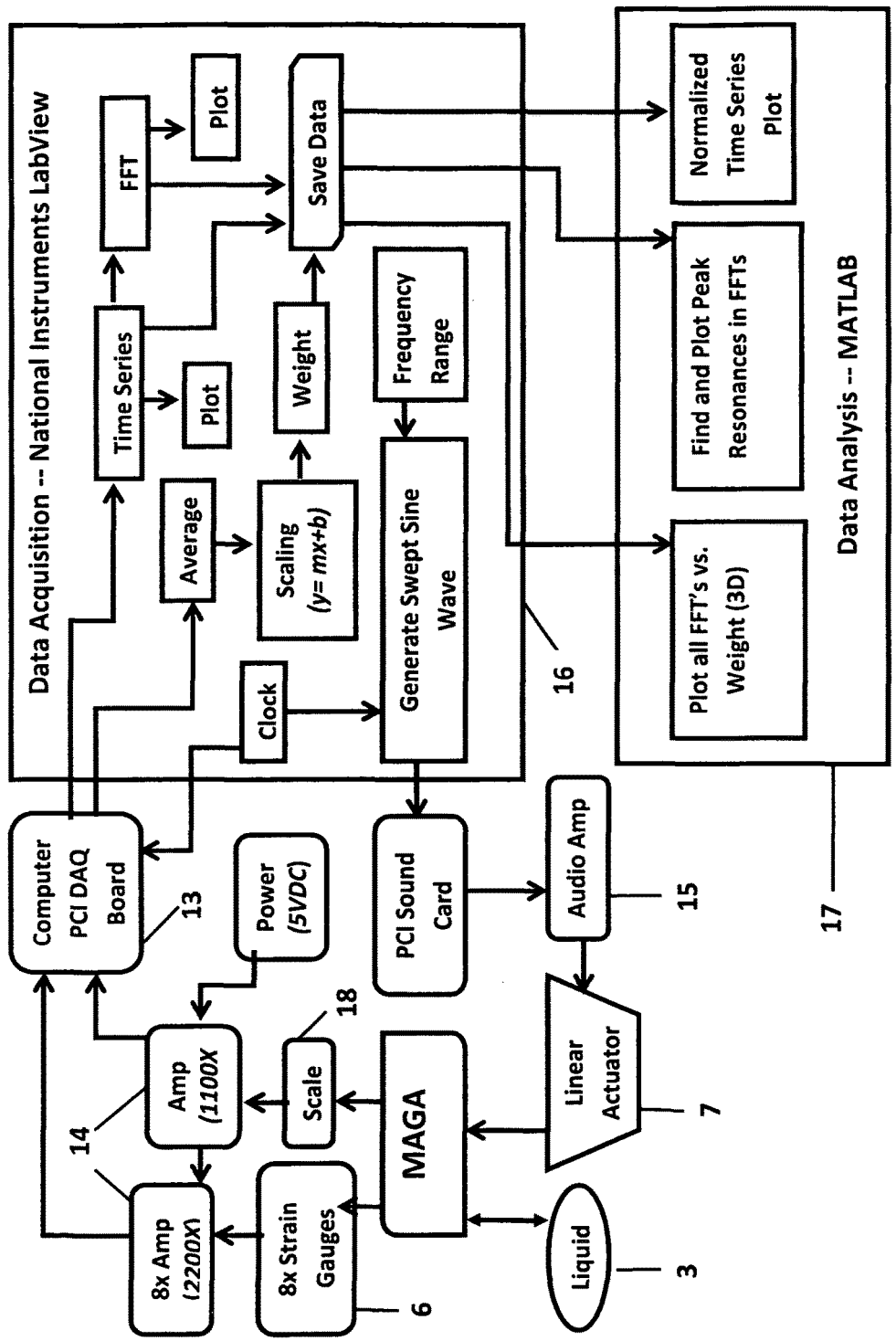
Figure 2. MAGA Block Diagram

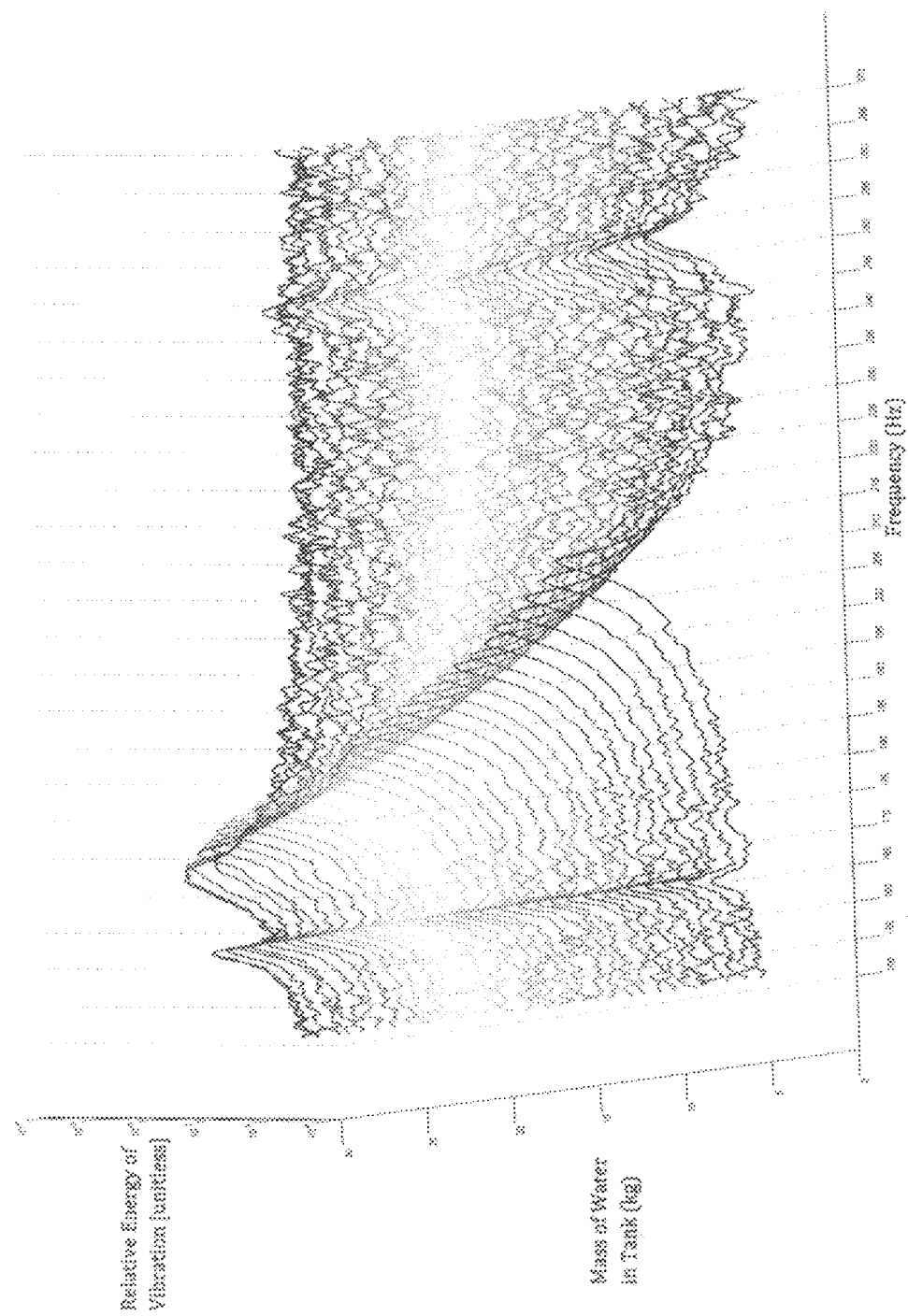
FIGURE 3. 3-D plot of MAGA laboratory resonant frequency and amplitude (energy) mode data vs. fluid (water) mass.

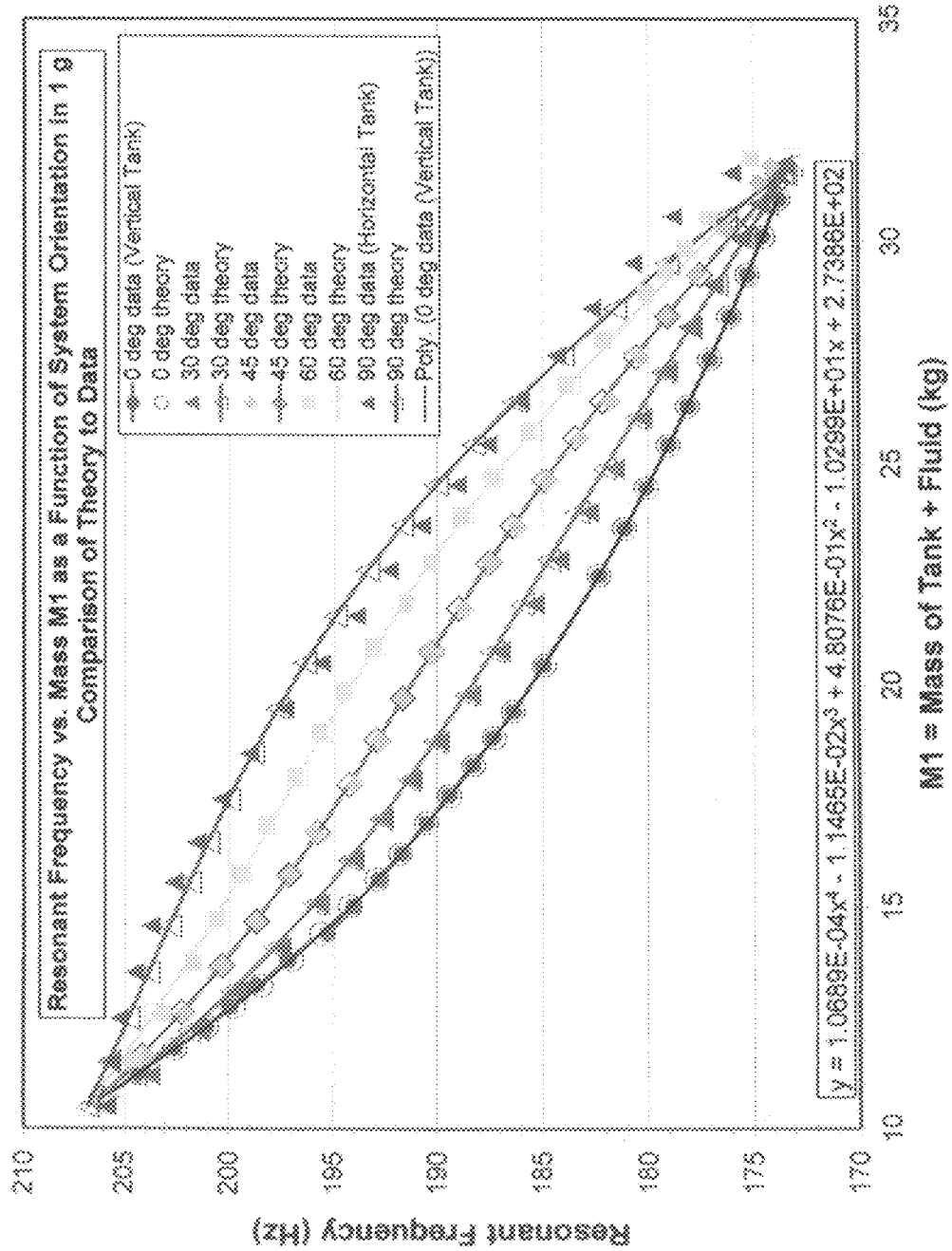
FIGURE 4. MAGLA laboratory resonant frequency data and theoretical curves vs. fluid (water) mass for several cylindrical fluid vessel symmetry-axis and excitation vector orientations with respect to the gravity vector.

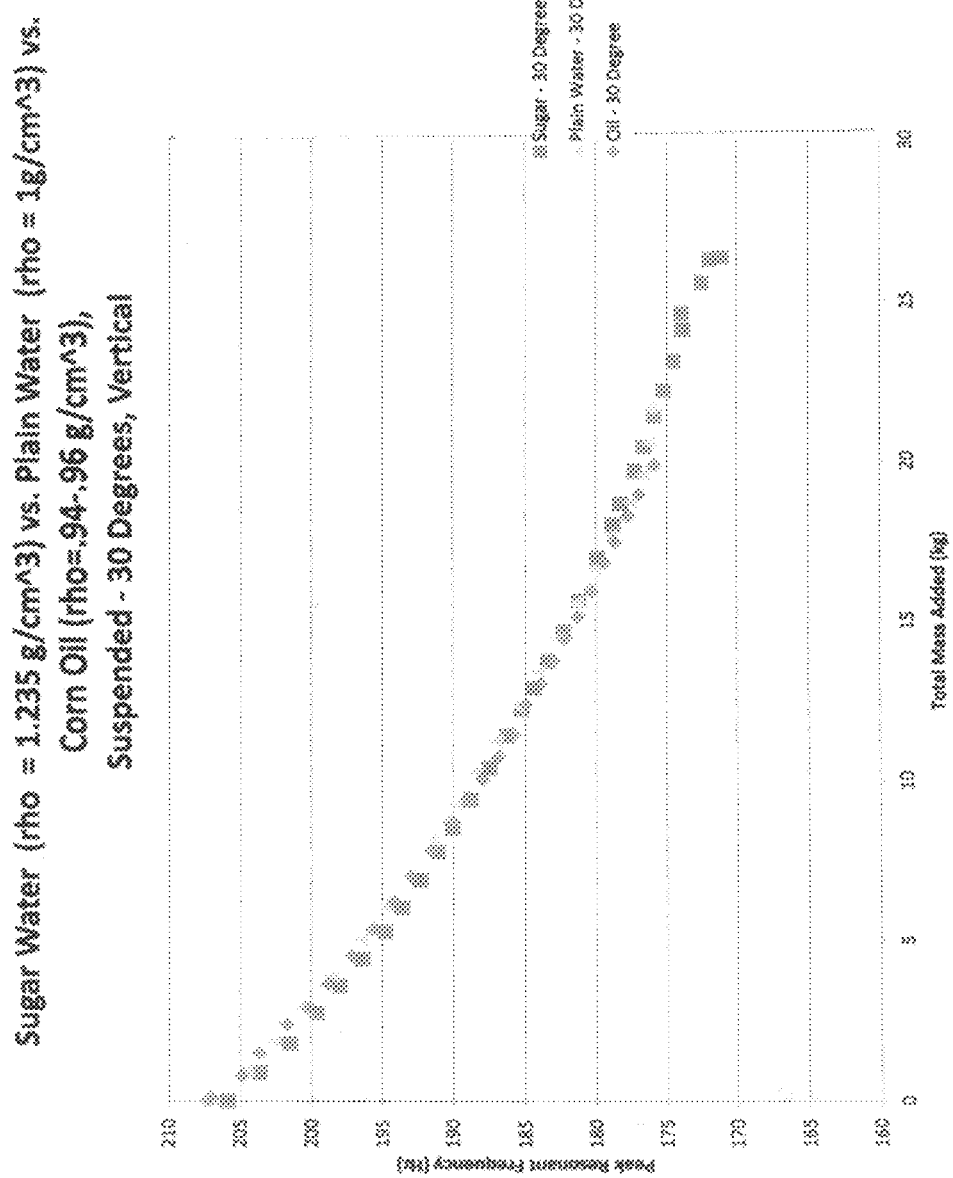
FIGURE 5. MAGA laboratory resonant frequency data vs. fluid mass for three different fluids having different densities and secondary properties, where the cylindrical fluid vessel symmetry-axis is positioned at an orientation angle of 30 degrees with respect to the gravity vector.

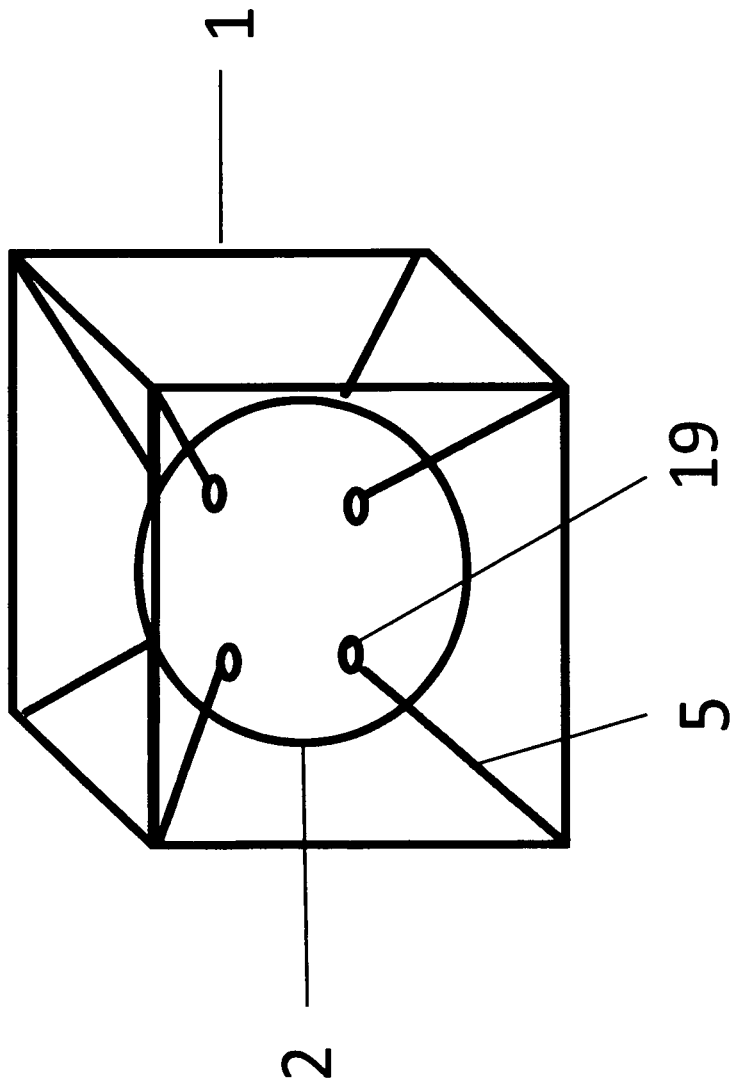
Figure 6. MAGA Perspective drawing of a spherical vessel 2 and its support structure comprising an open cubical frame 1 and eight symmetrically positioned support struts 5 with tension adjustments 19.

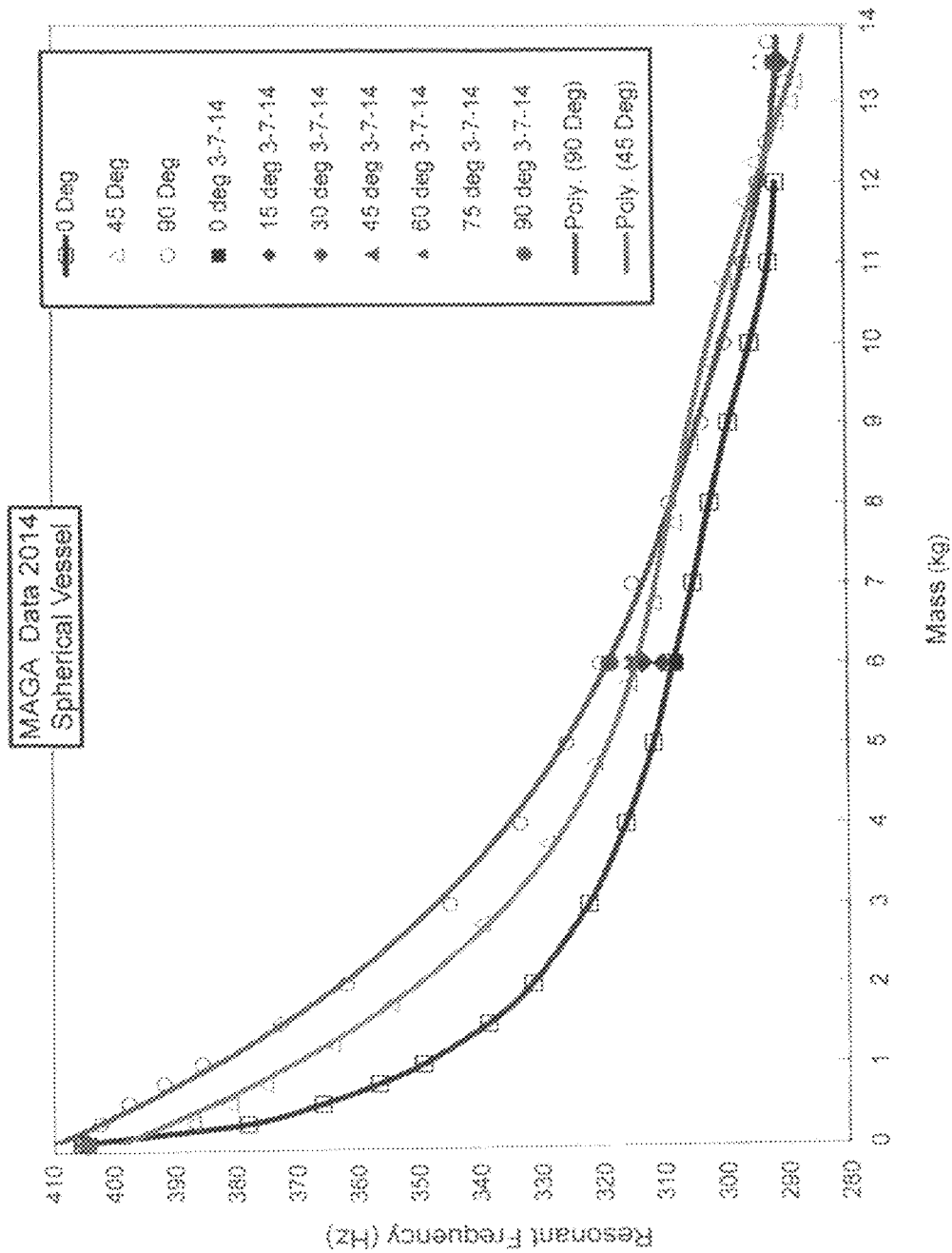
FIGURE 7. MAGA laboratory resonant frequency data vs. fluid (water) mass for several spherical fluid vessel excitation vector orientations with respect to the gravity vector.

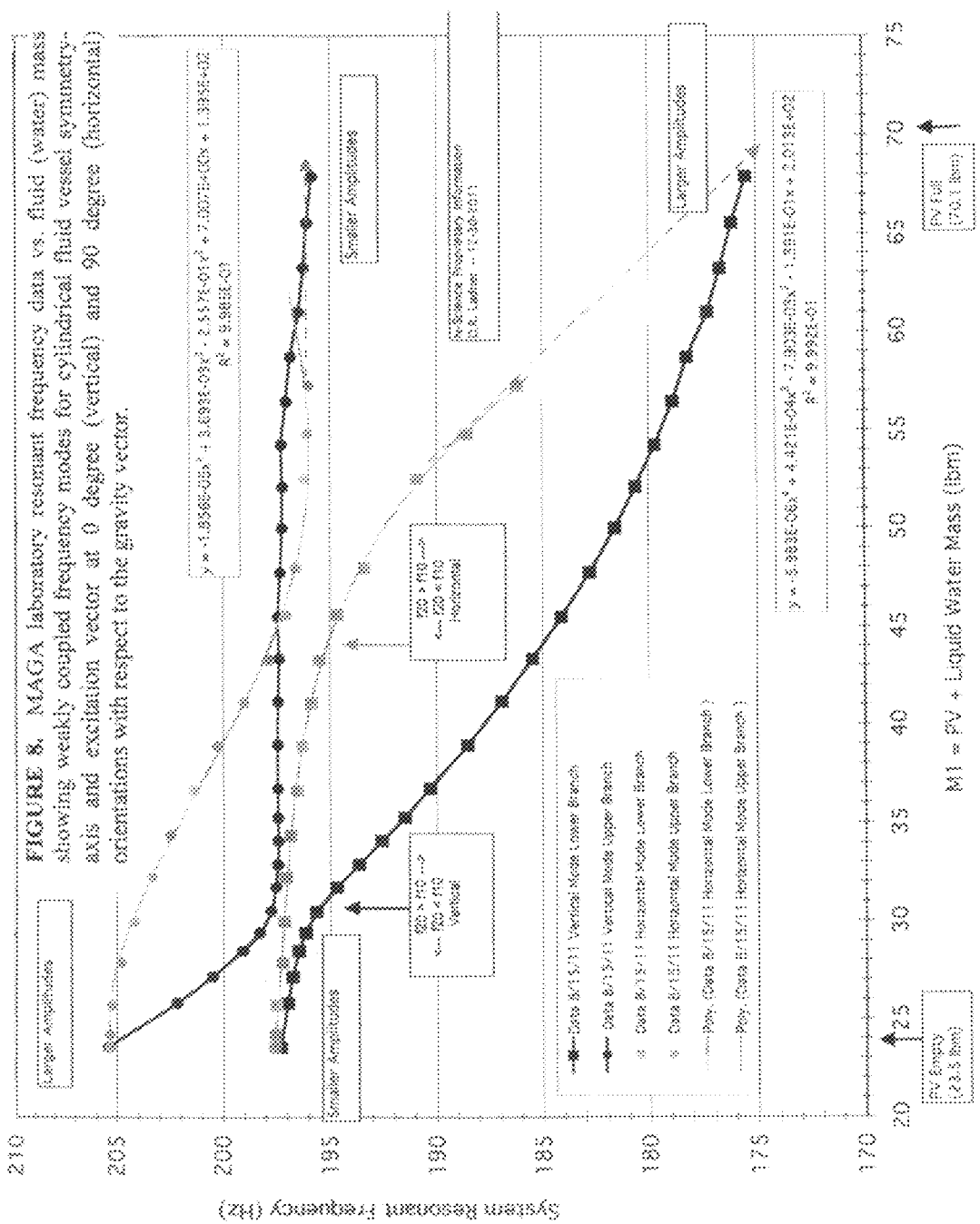

APPARATUS FOR GAUGING LIQUID OR SOLID MASS CONTAINED IN A VESSEL AND METHOD FOR USING SAME

CROSS-REFERENCE TO RELATED PATENT APPLICATION

The present application claims the benefit of U.S. Provisional Patent Application No. U.S. 61/852,184, filed Mar. 15, 2013. The entire contents of this provisional patent application are hereby incorporated by reference herein.

FIELD OF THE INVENTION

The invention described herein, Apparatus for Gauging Liquid or Solid Mass Contained in a Vessel and Method for Using Same (MAGA), is an electro-mechanical configuration designed to use mechanical resonance vibration frequencies and/or amplitudes to determine the mass of a fluid containment vessel or tank including its liquid, multi-phase, or solid contents. It does so by providing a swept frequency excitation and measuring the system resonance response using any of several detection methods. The field therefore involves fluid mass gauging in general, including specifically low gravity aerospace applications, using system resonance phenomena.

BACKGROUND OF THE INVENTION

The problem of determining fluid mass in a micro-g space environment is not a new one. During the past 60 years there have been several methods proposed. Considerable development effort has been expended to demonstrate some of these methods. In all cases the methods involve some secondary characteristic property of the system or comparison mass to deduce the unknown mass. Unfortunately, nearly every method requires fluid-specific calibrations as a direct result of relying on secondary physical properties. Some methods lose resolution as the fluid mass approaches depletion, when the residual quantity information is most useful.

The methods that have received the greatest attention in recent years include Pressure-Volume-Temperature (PVT); Propellant Gauging System (PGS); Capacitance Probes; Optical Mass Gauge Sensor (OMGS); and Book-Keeping Method. These can be summarized briefly as follows:

The PVT method determines the ullage volume and by deduction the liquid volume and mass. The method uses a reciprocating mechanical plunger/bellows to pressurize the fluid. Equilibrium thermodynamic relations are used to compute the volume based on system pressure and temperature data. The assumption of ullage temperature uniformity is required for accuracy and this condition is not always achievable in large vessels (e.g., LH2) or near liquid depletion when the ullage is large and the pressure decreases. Non-condensable GHe is also required for cryogenic fluids. Empirical corrections and fluid-specific thermophysical data are also required. An uncertainty of ~5% may be achievable with some fluids (LO2).

The PGS method uses a heat pulse technique similar to the heat pulse method used for successfully gauging superfluid helium in 1 g. It attempts to determine the thermal capacitance of the residual liquid. However, the low thermal conductivity of classical fluids results in special gauging corrections, and there may be uncertainty in the heater power, fluid temperature uniformity, and the external temperature environment. A mission unique thermal model of the vessel is required in addition to calibration curves.

The capacitance method relies on the dielectric constant properties of the fluid and vapor. A coaxial capacitance probe must always be calibrated for each vessel. It requires that the fluid be settled to define a flat interface and has typically been used in conjunction with low-level thrusting. It may be applicable in zero-g if the vessel internal vane arrangement is designed to achieve the desired interface profile, but this is not a simple matter. Uncertainty may arise from liquid meniscus effects. A similar capacitance geometry has been employed with slush hydrogen measurements.

The OMGS method has been described for solid and liquid hydrogen (LH2). It uses the vessel internal surface as an "integrating sphere" to obtain light transmittance data. Calculation of the attenuation factor leads to the mass determination. This method requires exacting knowledge of the optical absorption characteristics of the fluid, precision laser tuning and bandwidth, thermal regulation of the laser, and special coating of the vessel internal surface. Because every fluid has different attenuation properties, the method must be customized for each fluid.

The book-keeping method is a quasi-direct approach to mass gauging. Simply stated, it tracks the fluid outflow and in principle provides the residual mass if the initial mass value is known. In the case of vented vessels that employ vapor-cooled shields, low pressure loss/high sensitivity volumetric flow-metering requires corrections for pressure and temperature to accurately determine mass flow rate. Fluid specific calibration corrections are also required. For actual fluid transfer uncertainty arises from the possibility of two-phase flow or from over-ranging the flow meter. Uncertainty increases toward fluid depletion due to error accumulation.

Only recently has the resonant frequency approach received much attention. Rudy Werlink at NASA/KSC, in collaboration with Carthage College, has developed a gauging system that uses modal analysis. To our knowledge the project has flown on two missions in 2011 and 2012 on the NASA research aircraft that provides a few minutes of low g experiment time during its parabolic flight trajectories. Flight test data shown in FIG. 6 of reference 6 are much more linear than the lab data presented in that figure. Two important points should be made when comparing that research to the MAGA invention: 1) our design and earliest (unfunded) proposal to NASA pre-dates the KSC project, and 2) the fundamental approach of MAGA differs from that of NASA-KSC in that we are not trying to measure intrinsic oscillations of the stand-alone vessel/fluid proper, but rather as it constitutes a subsystem of the overall vessel-fluid-support structure, as shown in FIG. 1. The NASA/KSC approach is much more complicated and difficult to implement because many intrinsic modes, both mechanical and acoustical, are likely to exist as a function of the fluid distribution. This situation is eliminated when the fluid-containing vessel is coupled to a support structure via struts, rods, tubes, straps or other tension or compression linkages and the resonance data are analyzed as a simple in-situ spring/mass resonant system.

A cantilever spring/mass system for determining an unknown solid or fluid mass has been described by Jun Isobe et al. (Ref. 7). There are several significant differences between that invention and the present invention: 1) it requires a single cantilever and a test mass to determine the spring constant in a one degree of freedom constraint; 2) to measure a fluid mass it requires a bellows and/or bladder to position the fluid; 3) it is primarily used to measure small experimental masses on the ISS; 4) it uses a "pinger" to excite natural resonance, as opposed to the MAGA swept frequency excitation (forced resonance); 5) it does not incorporate resonant amplitude (energy) data as part of the mass determination (see FIG. 3 of this application); 6) it is not applicable to any practical cryogenic fluid vessel which involves an extensive strut or strap support system to reduce parasitic heat leaks.

In summary, most of the foregoing fluid gauging methods have drawbacks that are directly associated with the fact that secondary fluid properties are required to determine mass, and fluid-specific calibrations or modifications are usually required. By contrast MAGA uses the defining property of mass itself to make this determination, viz., the resonant response of the mass in both frequency and amplitude to an applied oscillatory force. The MAGA method is implemented in situ and does not require additional test masses or external measuring apparatus.

SUMMARY OF THE INVENTION

The invention described herein, Apparatus for Gauging Liquid or Solid Mass Contained in a Vessel and Method for Using Same (MAGA), and referred to herein as MAGA, is an invention that provides a means for measuring an unknown quantity or mass of a fluid or solid contained in a storage vessel, or fuel vessel, having application to terrestrial (one-g) and zero gravity (zero-g) or microgravity (micro-g) environments. In micro-g environments the fluid cannot be weighed directly, and its location within the vessel may be dominated by surface tension effects so that other conventional measurement methods, such as the height of the free surface above the bottom of the vessel or the vessel weight, are inapplicable. Examples of space applications are orbiting supply depots or rocket propulsion fuel vessels when the rocket is coasting. The invention measurement method is also applicable to a one-g earth environment, as in the case of terrestrial fluid storage vessels. Terrestrial applications include remote sensing of fluid quantities in liquid storage vessels or fuel vessels in the field, for example, vessels containing cryogenic fluids such as LN2 or liquefied natural gas (LNG). Other aerospace applications include measurements of fluid mass in lunar or planetary ground storage vessels.

BRIEF DESCRIPTION OF THE DRAWINGS

FIG. 1a is a generic thawing of the side view of a cylindrical vessel showing the primary mechanical components and devices for frequency excitation and measurement.

FIG. 1b is a generic drawing of the end view of a cylindrical vessel or the top, side, or end view of a spherical vessel showing the primary mechanical components and devices for frequency excitation and measurement.

FIG. 2 is a block diagram of one arrangement of the MAGA data acquisition and analysis systems.

FIG. 3 shows a 3D plot of MAGA resonant frequency and amplitude (energy) modes vs. fluid mass as recorded in one laboratory experimental run using water.

FIG. 4 shows MAGA resonant frequency data vs. fluid mass for several cylindrical fluid vessel orientations with respect to the gravity vector as recorded in several laboratory experimental runs using water.

FIG. 5 shows MAGA resonant frequency data vs. fluid mass for three different fluids having different densities and secondary properties, where the cylindrical fluid vessel is positioned at an orientation angle of 30 degrees with respect to the gravity vector.

FIG. 6 is a MAGA perspective drawing of a spherical vessel and its support structure comprising a cubical frame and eight symmetrically positioned support struts.

FIG. 7 shows MAGA resonant frequency data vs. fluid mass for several spherical fluid vessel orientations with respect to the gravity vector as recorded in several laboratory experimental runs using water.

FIG. 8 shows MAGA resonant frequency data vs. fluid mass for two weakly coupled modes for a cylindrical vessel in two orientations with respect to the gravity vector as recorded in several laboratory experimental runs using water.

DETAILED DESCRIPTION OF THE INVENTION

The basic physical principle of the Apparatus for Gauging Liquid or Solid Mass Contained in a Vessel and Method for Using Same (MAGA) is the detection of a resonant frequency vibration mode or modes associated with the spring/mass system when an excitation source is present. The excitation produces a relative displacement between the fluid containment vessel and its support frame or other fixture to which it is fastened. The displacement produces a signal voltage in one or more of the sensors, such as strain gauge devices or accelerometers, which are attached to the fluid containment vessel or its physical supports. The amplitude of the sensor signal varies in substantial accordance with known physical principles that relate the amplitude of vibration to the frequency of vibration in spring/mass systems. Both the amplitude and frequency of the resonant vibrations can be used to determine the unknown quantity or mass of the fluid in the fluid containment vessel unambiguously because the frequency-mass relationship is monotonic.

Alternatively, a means for determining the resonant frequency as measured from the observation of the displacement vs. time, for example, using a laser positioning device, can be used. In contrast with other low-g mass gauging methods that typically require an accurate knowledge of the secondary properties of the fluid, this method uses fundamental physical principles that relate the observed resonant vibration modes directly to the system masses. Therefore, for a given mass of fluid in the fluid containment vessel, the resulting amplitudes and resonant frequency modes are identical even if the fluid secondary properties are different. Such secondary properties might include, for example: density, surface tension, thermal conductivity, or viscosity, all or some of which may depend on the fluid temperature or pressure. This fluid-independent behavior has been confirmed in laboratory experiments conducted during 2012, and is shown in FIG. 5 of the present invention.

The invention is also applicable to a subliming solid such as, for example, solid nitrogen. In such systems the sublimation that results from parasitic heat leaks or from sublimation due to active cooling of an instrument reduces the solid mass over time. The invention is also applicable to a fluid at its triple point comprising all three phases. Accurate determination of the residual solid or triple-point three-phase mass is necessary for planning the instrument activity timeline. It should be appreciated that the term "fluid" as referred to regarding this invention includes any substance in its multiple phases as determined by ambient temperature and pressure values.

The analysis of a three-mass, two-spring system gives angular resonant frequency solutions as follows:

$$\omega_o^4 - \omega_o^2[k_{12}(M_1+M_2)/M_1+M_2+k_{23}(M_2+M_3)/M_2M_3] + k_{12}k_{23}(M_1+M_2+M_3)/M_1M_2M_3 = 0 \quad (1)$$

for which the quadratic formula solution for the squared angular frequency $\omega_o^2$ gives two longitudinal modes, symmetrical and anti-symmetrical with respect to the center of mass. A symmetrical transverse mode also exists for the 3-mass configuration, and this mode can be excited (having very low amplitude) if the vessel supports are not precisely balanced, even when the initial displacement is along the vessel symmetry axis.

For the special case where $M_3 \gg M_1$ and $M_2$, Equation (1) reduces to $$\omega_o^4 - \omega_o^2[k_{12}(M_1+M_2)/M_1+M_2+k_{23}/M_2] + k_{12}k_{23}/M_1M_2 \quad (2)$$

For a 2-mass configuration comprising only the vessel and frame ($k_{23}=0$), the solution is $$\omega_o = [k_{12}(M_1+M_2)/M_1M_2]^{1/2} \quad (3)$$

For the special case where $M_2 \gg M_1$, Equation (3) reduces to the familiar simple harmonic oscillator result $$\omega_o[k_{12}/M_1]^{1/2} \quad (4)$$

Analytical model results using these formulas with various fluids show that the vessel-fluid-support structure resonant modes for total masses of about 20 to 100 kg typically fall within the 50 Hz to 1 kHz range. Other variations of these formulas and associated frequency ranges are possible, including coupling between different frequency modes, as shown in FIG. 8, and are within the scope of the present disclosure.

FIGS. 1a and 1b show the components of typical MAGA systems in two different views. Although they represent distinct cylindrical and spherical vessel geometries, any vessel geometry will resonate in accordance with spring/mass equations describing small vibrations. It should be appreciated that the particular implementations and geometries shown and described herein are not intended to otherwise limit the scope of the present invention. In FIGS. 1a and 1b the vessel primary support structure, shell, or frame 1 is connected to the vessel 2 by a system of struts, tension straps, rods, or tubes 5. In a micro-g or zero-g environment a fluid or multi-phase substance 3 of unknown mass is in contact with the vessel internal wall by means of surface tension, in which a system of vanes or baffles 13 may exist to augment the contact. Ullage (vapor) 4 is typically not in contact with the vessel wall. Component 3 may also represent a sublimating solid, such as solid N2, or a triple point three-phase substance.

Excitation of the system is provided by linear actuators 7, such as voice coils or similar electro-mechanical devices, which are driven over an applicable range of swept frequency. Sensors 6, located on the supports 5, such as strain gauges or similar devices, measure the amplitude and frequency of the oscillations induced by the excitation. Component 8 represents a laser positioning device or other means for directly measuring the induced relative or absolute displacements between the vessel and its support structure. Component 9 represents a means for inducing excitations directly to the vessel primary support structure, shell, or frame 1 rather than to the vessel 2 itself. In cases where the system, comprising components 1 to 9, is in turn attached to a depot or bulwark 10, comprising a more complex system such as that described in Equation 1), additional support members 11 and sensors 12 are included in the measurement. It should be appreciated that omissions of implementations of this invention involving additional masses, geometries, spring supports, and configurations, not shown in FIGS. 1a and 1b or in FIG. 6, and not specifically described herein, are not intended to otherwise limit the scope of the present invention.

FIG. 2 shows one version of the MAGA data acquisition and analysis system used successfully as an invention measurement method in laboratory experiments. It comprises several principal components, including but not limited to, PC computer/controller 13, strain gauge sensors 6 and low noise amplifiers 14, linear actuators 7 for system excitation, audio amplifier 15, and LabVIEW 16 for producing swept sine wave excitation and acquiring signal acquisition with Fast Fourier Transform (FFT), and MATLAB 17 software for data analysis and plotting. During testing calibration of the test mass is made using a digital scale 18 with output to the PC. Other variations of this data acquisition and analysis system are possible and are within the scope of the present disclosure.

FIG. 3 is a 3D plot of Fast Fourier Transforms (frequency in Hz) and relative resonance amplitudes (energies) vs. fluid (water) mass (kg) for the MAGA mass gauging system and is a typical representation of laboratory data acquired. This plot represents the frequency spectrum of the vessel at different fill levels, i.e., fluid masses. It is seen in the central mode (~170 Hz to ~210 Hz) that the peak resonant frequency decreases and the resonance amplitude increases as fluid mass is increased.

FIG. 4 is a 2D plot of the peak resonant frequencies for different masses and orientations of the vessel with respect to the gravity vector. This chart demonstrates generally that the system resonant frequency decreases monotonically with increasing fluid mass for measurements in all orientations. It also shows the clean and precise nature of the invention data acquisition system and signal processing method. Note that resonant frequency is different for different system orientations in a laboratory (1 g) environment, thereby generating a family of curves. These data curves converge at their end points. This behavior can be understood in terms of the vessel-fluid centroid, which is located along the vessel symmetry/excitation force vector axis and at the center of the vessel for empty vessel and full vessel conditions, regardless of vessel orientation. It is off the vessel symmetry/excitation force vector axis for a partially full cylindrical vessel at any non-vertical orientation angle.

For a geometrically symmetric vessel the resonant frequency vs. mass is analytically modeled with a single adjustable parameter 8 as:

$$\omega = \omega_o[1+\beta(1-\beta)^*\{\sin(\varphi/\delta)^{\wedge}2\}] \quad (5)$$

where $\omega_o$ is the vertical orientation angular frequency, $\beta$ is the fluid fraction, $\delta$ is a geometry-dependent constant, and $\varphi$ is the angle between the excitation vector (or cylindrical symmetry axis) and the gravity vector. For a cylindrically-symmetric vessel, $\delta \sim 2$, and for a spherically-symmetric vessel, $\delta \sim 3$.

In any known vessel orientation the frequency to mass relationship is 1 to 1, i.e., the curves are monotonic such that no double-valued relation exists, and the mass is unambiguously determined. In a micro-g or zero-g environment in which the fluid is symmetrically distributed within the vessel, the centroid remains centered and the curve family in FIG. 4 degenerates into a single curve independent of the excitation vector.

FIG. 5 shows the independence of the resonant frequency vs. fluid mass from fluid type for three fluids of different density and secondary properties. The data were obtained at a vessel orientation of 30 degrees using a cylindrically-symmetric fluid vessel. Similar results were obtained at other orientation angles.

FIG. 6 shows one preferred embodiment of the vessel-fluid-support structure in a perspective drawing. The support structure 1 comprises a cubical frame and eight symmetrically positioned support struts 5 supporting a spherical vessel 2. The solid support struts, tubes, or rods 5 have tension/compression adjustment devices 19.

FIG. 7 shows typical resonant frequency vs. fluid mass data for various excitation force vector orientations of a spherical vessel with respect to the gravity vector. The data show behavior in a 1 g environment similar to the data in FIG. 5, in that there exists a family of monotonic curves. But here the centroid remains in a fixed location along the gravity vector, for a given fluid mass, independent of vessel orientation. Since the excitation force vector does not generally pass through the vessel-fluid centroid, except in the empty and full vessel conditions, the resonance curves obey Equation (5) with $\delta \sim 3$.

It is possible that more than one resonant branch may be measured, e.g., in the case of two weakly coupled modes, as shown in FIG. 8. In such cases the sum frequency of the two branches is also found to be monotonic, so that the unknown fluid mass can be unambiguously determined. In FIG. 8 a fixed frequency mode at ~197 Hz crosses the 0 degree (vertical) orientation mode (lowest curve in FIG. 4) at a vessel-fluid combined mass of ~14 kg (~31 lbm) to generate the two branches shown in darker symbols. Likewise it crosses the 90 degree (horizontal) orientation mode (uppermost curve in FIG. 4) at a vessel-fluid combined mass of ~20 kg (~44 lbm) to generate the two branches shown in lighter symbols. Mathematical relationships for coupled frequencies and relative amplitudes are given, e.g., in Ref 2, pp. 188-198.

The following references are hereby incorporated by reference herein as supportive background information regarding the invention:
1. *Mechanics, Volume 1, $2^{nd}$ Edition*, L. D. Landau and E. M. Lifshitz, Pergamon Press, Oxford, Addison-Wesley Publishing Company, Inc., Reading, M A, 1969.
2. *Mechanics, $2^{nd}$ Edition*, Keith R. Symon, Addison-Wesley Publishing Company, Inc., Reading, M A, 1960.
3. *Lagrangian Dynamics*, Dare A. Wells, Schaum Publishing Co., New York, 1967.
4. *Theoretical Mechanics*, Murray R. Spiegel, Schaum Publishing Co., New York, 1967.
5. *Physics*, Robert Resnick, David Halliday, and Kenneth S. Krane, John Wiley and Sons, Inc., New York, 1992.
6. Rudy Werlink et al., "Modal Evaluation of Fluid Volume in Spacecraft Propellant Vessels", NASA Internal Technical Note, 2011
7. U.S. Pat. No. 6,756,548, Jun Asobe et al., Jun. 29, 2004

What is claimed is:
1. A mass gauging apparatus comprising
   a) a vessel-fluid-support structure, further comprising:
      i) a vessel of arbitrary geometry containing a fluid or solid of unknown mass in contact with said vessel,
      ii) a vessel support structure of arbitrary geometry supporting said vessel,
      iii) vessel supports of arbitrary geometry connecting said vessel to the vessel support structure,
   b) sensors located on the vessel, the vessel support structure, and/or the vessel supports,
   c) an excitation device providing periodic or aperiodic vibrations to the vessel-fluid-support structure,
   d) a data acquisition system electrically configured to said excitation device and said sensors, determining one or more resonant frequency modes of the vessel-fluid-support structure and the relative amplitudes of same, and
   e) a data analysis system, selectively identifying and plotting resonant frequency mode features as a function of the fluid or solid mass.

2. The apparatus of claim 1 wherein the data acquisition system comprises sensor output amplification, signal averaging, and a Fast Fourier Transform capability with programmable time resolution.

3. The apparatus of claim 2 wherein the data analysis system comprises three dimensional plotting of frequency, mass, and amplitude; peak resonance discrimination; and normalized time series plotting.

4. The apparatus of claim 3 wherein the excitation device provides a swept frequency excitation over a frequency range inclusive of resonant frequency modes of the vessel-fluid-support structure.

5. The apparatus of claim 4 wherein the fluid or solid of unknown mass is a multi-phase fluid or a sublimating solid.

6. The apparatus of claim 4 wherein the vessel is a symmetrical geometric figure.

7. The apparatus of claim 4 wherein the vessel support structure is a symmetrical geometric figure.

8. The apparatus of claim 4 wherein the vessel supports comprise at least one rod, strut, tube, or strap, comprising an arrangement of connecting members and establishing unique resonant frequencies of the vessel-fluid-support structure.

9. The apparatus of claim 4 wherein the vessel supports have tension or compression adjustments.

10. The apparatus of claim 4 wherein the vessel internal space contains a network of vanes, baffles, or porous surface structure providing additional surface area for fluid containment in a micro-gravity environment.

11. The apparatus of claim 4 wherein the excitation device is at least one linear actuator, voice coil, piezoelectric or similar device capable of providing oscillatory mechanical motion.

12. The apparatus of claim 4 wherein the sensors are strain gauges.

13. The apparatus of claim 4 wherein the sensors are accelerometers.

14. The apparatus of claim 4 wherein the sensors are laser positioning devices.

15. A method for determining in situ the unknown mass of a fluid or solid contained in a vessel, comprising four sequential steps, wherein said sequential steps are performed in the order listed:
   1) first, applying vibrations with a swept frequency or other excitation device, to one or more components of a vessel-fluid-support structure;
   2) second, acquiring, with a data acquisition system configured with said vessel-fluid-support structure and its associated sensor(s):
      a) one or more resonant frequency modes of said vessel-fluid-support structure, and
      b) relative amplitude(s) of said mode(s) of the vessel-fluid-support structure;
   3) third, identifying, storing, and plotting resonant frequency mode features with a data analysis system configured with said vessel-fluid-support structure and said data acquisition system; and
   4) fourth, comparing pre-determined frequency-mass, amplitude-mass, or frequency-amplitude-mass relationships to determine the unknown fluid or solid mass, including calibration curves, data bases, and lookup tables.

16. The method of claim 15 wherein the four sequential steps are computer controlled.

17. The method of claim 16 wherein the excitation device, the data acquisition system, and the data analysis system components are configured to operate sequentially and autonomously in a micro-gravity environment.

18. The method of claim 17 wherein the fluid or solid of unknown mass is a multi-phase fluid or a sublimating solid.

19. The method of claim 17 wherein the excitation is sinusoidal.

20. The method of claim 17 wherein the excitation is aperiodic.

* * * * *